(12) United States Patent
Govari et al.

(10) Patent No.: US 12,048,495 B2
(45) Date of Patent: Jul. 30, 2024

(54) LOCATION PAD WITH IMPROVED IMMUNITY TO INTERFERENCE

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/081,764

(22) Filed: Dec. 15, 2022

(65) Prior Publication Data

US 2023/0113226 A1    Apr. 13, 2023

Related U.S. Application Data

(63) Continuation of application No. 15/855,265, filed on Dec. 27, 2017, now Pat. No. 11,612,437.

(Continued)

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 90/30* (2016.02); *A61B 90/50* (2016.02);
(Continued)

(58) Field of Classification Search
CPC ......... A61B 34/20; A61B 5/062; A61B 90/30; A61B 90/50; A61B 17/24;
(Continued)

(56) References Cited

U.S. PATENT DOCUMENTS 5,309,913 A    5/1994 Kormos et al.
5,391,199 A    2/1995 Ben-Haim
(Continued)

FOREIGN PATENT DOCUMENTS

CN    106333750 A    1/2017
JP    H08-71086 A    3/1996
(Continued)

OTHER PUBLICATIONS

Barratt, Dean C., et al. "Optimisation and evaluation of an electromagnetic tracking device for high-accuracy three-dimensional ultrasound imaging of the carotid arteries." *Ultrasound in medicine & biology* 27.7 (2001): 957-968.
(Continued)

*Primary Examiner* — Sanjay Cattungal
(74) *Attorney, Agent, or Firm* — Frost Brown Todd LLP

(57) ABSTRACT

A location pad includes multiple field-generators, a frame and a mounting fixture. The multiple field-generators are configured to generate respective magnetic fields in a region-of-interest of a patient body, for measuring a position of a medical instrument in the region-of-interest. The frame is configured to fix the multiple field-generators at respective positions surrounding the region-of-interest. The mounting fixture is configured to position the frame above the patient body.

18 Claims, 2 Drawing Sheets

Related U.S. Application Data

(60) Provisional application No. 62/504,404, filed on May 10, 2017.

(51) Int. Cl.
  *A61B 90/30* (2016.01)
  *A61B 90/50* (2016.01)
  *A61B 17/00* (2006.01)
  *A61B 17/24* (2006.01)

(52) U.S. Cl.
  CPC ........... *A61B 2017/00199* (2013.01); *A61B 2017/00725* (2013.01); *A61B 17/24* (2013.01); *A61B 2034/2051* (2016.02); *A61B 2090/309* (2016.02)

(58) Field of Classification Search
  CPC ......... A61B 2017/00199; A61B 2017/00725; A61B 2034/2051; A61B 2090/309; A61B 2017/3413
  See application file for complete search history.

(56) References Cited

U.S. PATENT DOCUMENTS

| | | | |
|---|---|---|---|
| 5,831,260 | A | 11/1998 | Hansen |
| 6,239,724 | B1 | 5/2001 | Doron et al. |
| 6,332,089 | B1 | 12/2001 | Acker et al. |
| 6,366,799 | B1 | 4/2002 | Acker et al. |
| 6,484,118 | B1 | 11/2002 | Govari |
| 6,618,612 | B1* | 9/2003 | Acker .................... A61B 90/36 128/899 |
| 6,690,963 | B2 | 2/2004 | Ben-Haim et al. |
| 8,421,569 | B1* | 4/2013 | He ......................... H01F 7/202 335/284 |
| 2002/0065455 | A1 | 5/2002 | Ben-Haim et al. |
| 2003/0120150 | A1 | 6/2003 | Govari |
| 2003/0200052 | A1 | 10/2003 | Seiler et al. |
| 2004/0147839 | A1* | 7/2004 | Moctezuma de la Barrera .......... A61B 34/20 600/429 |
| 2004/0068178 | A1 | 10/2004 | Chang et al. |
| 2006/0004286 | A1 | 1/2006 | Chang et al. |
| 2007/0094798 | A1* | 5/2007 | Yu .......................... A61G 13/10 5/507.1 |
| 2007/0260296 | A1* | 11/2007 | Porter ..................... A61N 5/062 607/88 |
| 2007/0265526 | A1* | 11/2007 | Govari .................... A61B 34/20 600/424 |
| 2008/0009713 | A1 | 1/2008 | Tuma |
| 2011/0072586 | A1* | 3/2011 | Yu ......................... A61G 13/105 5/623 |
| 2013/0318714 | A1* | 12/2013 | Yu .......................... A61B 90/60 5/507.1 |
| 2014/0194734 | A1 | 7/2014 | Birkenbach et al. |
| 2015/0297303 | A1* | 10/2015 | Heindl ..................... A61B 6/04 600/424 |
| 2016/0008083 | A1* | 1/2016 | Kesten ................... A61B 5/062 600/424 |
| 2016/0331269 | A1* | 11/2016 | Kruger .................... A61B 90/14 |
| 2018/0310886 | A1* | 11/2018 | Salazar ................... A61G 15/12 |
| 2018/0325603 | A1 | 11/2018 | Govari et al. |

FOREIGN PATENT DOCUMENTS

| | | |
|---|---|---|
| JP | 2006-271520 A | 10/2006 |
| WO | WO 1996/005768 A1 | 2/1996 |
| WO | WO 2016/007591 A1 | 1/2016 |

OTHER PUBLICATIONS

Chinese Office Action and Search Report dated Aug. 22, 2022, for Application No. 201810443823.X, 10 pages.

European Search Report and Written Opinion dated Sep. 12, 2018, for Application No. 18176319.4, 7 pages.

Japanese Notification of Reasons for Refusal dated Mar. 15, 2022, for Application No. 2018-090422, 5 pages.

Japanese Final Office Action dated Sep. 27, 2022, for Application No. 2018-090422, 4 pages.

* cited by examiner

LOCATION PAD WITH IMPROVED IMMUNITY TO INTERFERENCE

CROSS-REFERENCE TO RELATED APPLICATIONS

This application is a continuation of U.S. application Ser. No. 15/855,265, filed Dec. 27, 2017, published as U.S. Pub. No. 2018/0325603, entitled "Location Pad with Improved Immunity to Interference," which claims the benefit of U.S. Provisional Patent Application 62/504,404, filed May 10, 2017, whose disclosure is incorporated herein by reference.

FIELD OF THE INVENTION

The present invention relates generally to position tracking systems, and particularly to methods and systems for improving the resilience of magnetic position tracking systems to magnetic interference.

BACKGROUND OF THE INVENTION

Magnetic position tracking systems are used in various medical procedures, such as in sinuplasty, and are required to withstand various types of interferences.

For example, U.S. Patent Application Publication 2003/0200052, issued as U.S. Pat. No. 6,836,745 on Dec. 28, 2004, whose disclosure is incorporated herein by reference, describes a method for determining the position of a sensor element, according to which a magnetic alternating field emitted by at least one field generating unit is measured. The inventive method is characterized in interference fields are calculated, preferably to a first approximation, said interference fields being caused by eddy currents produced in electrically conductive objects. The position that can be determined on the basis of the signal received in the sensor element is corrected on the basis of the calculated interference fields.

U.S. Patent Application Publication 2006/0004286, issued as U.S. Pat. No. 7,720,521 on May 18, 2010, whose disclosure is incorporated herein by reference, describes devices, systems and methods for performing image guided interventional and surgical procedures, including various procedures to treat sinusitis and other disorders of the paranasal sinuses, ears, nose or throat.

SUMMARY OF THE INVENTION

An embodiment of the present invention that is described herein provides a location pad including multiple field-generators, a frame and a mounting fixture. The multiple field-generators are configured to generate respective magnetic fields in a region-of-interest of a patient body, for measuring a position of a medical instrument in the region-of-interest. The frame is configured to fix the multiple field-generators at respective positions surrounding the region-of-interest. The mounting fixture is configured to position the frame above the patient body.

In some embodiments, the location pad includes one or more illumination elements, which are mounted in the frame and are configured to illuminate the patient body. In other embodiments, each of the illumination elements includes one or more light emitting diodes (LEDs). In yet other embodiments, the frame includes transparent material.

In an embodiment, the frame includes transparent material having expansion coefficient higher than $74*10^{-6}$ $[1/°K]$. In another embodiment, the mounting fixture is configured to reduce a level of interference caused to the magnetic field, by positioning the frame at a distance larger than 5 cm from a metallic part.

There is additionally provided, in accordance with an embodiment of the present invention, a method for producing a location pad, the method includes providing multiple field-generators, which generate respective magnetic fields in a region-of-interest of a patient body, for measuring a position of a medical instrument in the region-of-interest. The multiple field-generators are fixed on a frame, at respective positions surrounding the region-of-interest. The frame is positioned above the patient body using a mounting fixture.

The present invention will be more fully understood from the following detailed description of the embodiments thereof, taken together with the drawings in which:

DETAILED DESCRIPTION OF EMBODIMENTS

Overview

Embodiments of the present invention that are described hereinbelow provide improved techniques for reducing interference in magnetic position tracking systems.

Magnetic position tracking systems are used in various medical procedures, such as in sinuplasty procedures. In such systems, multiple field-generators that apply magnetic fields are mounted on a location pad. A sinuplasty tool that comprises a position sensor is inserted into the patient nose, and the position tracking system tracks the position of the sinuplasty tool using the position sensor, which is configured to detect the magnetic fields applied by the field-generators.

In some cases, a position tracking system may be surrounded by metallic parts and/or electrical signals that may interfere with the magnetic fields, and degrade the performance of the positioning system. For example, in sinuplasty procedures the patient typically sits in an operating chair comprising metallic parts. Furthermore, the location pad may comprise illumination elements that may interfere with the magnetic fields produced by the field-generators. For example, (i) these elements may be made from metallic parts and (ii) when lit up, these elements conduct electrical signals that may interfere with the magnetic fields.

In some embodiments, the location pad is mounted above the patient head so as to set the field-generators far away from the metallic parts of the operating chair. In an embodiment, a pillow that supports the patient head during the procedure, interposes between the location pad and the metallic parts of the chair, so as to further reduce the level of interference caused by the metallic parts of the chair.

In some embodiments, the location pad comprises illumination elements, such as light emitting diodes (LEDs).

During operation, the temperature of the field-generators may increase due to the electrical currents flowing therein. In an embodiment, the location pad comprises a frame, made from materials having low thermal expansion coefficient, such as Perspex®, which is transparent to pass the light from the LEDs and remains almost un-deformed even at relatively high temperatures.

System Description

Figure 1:
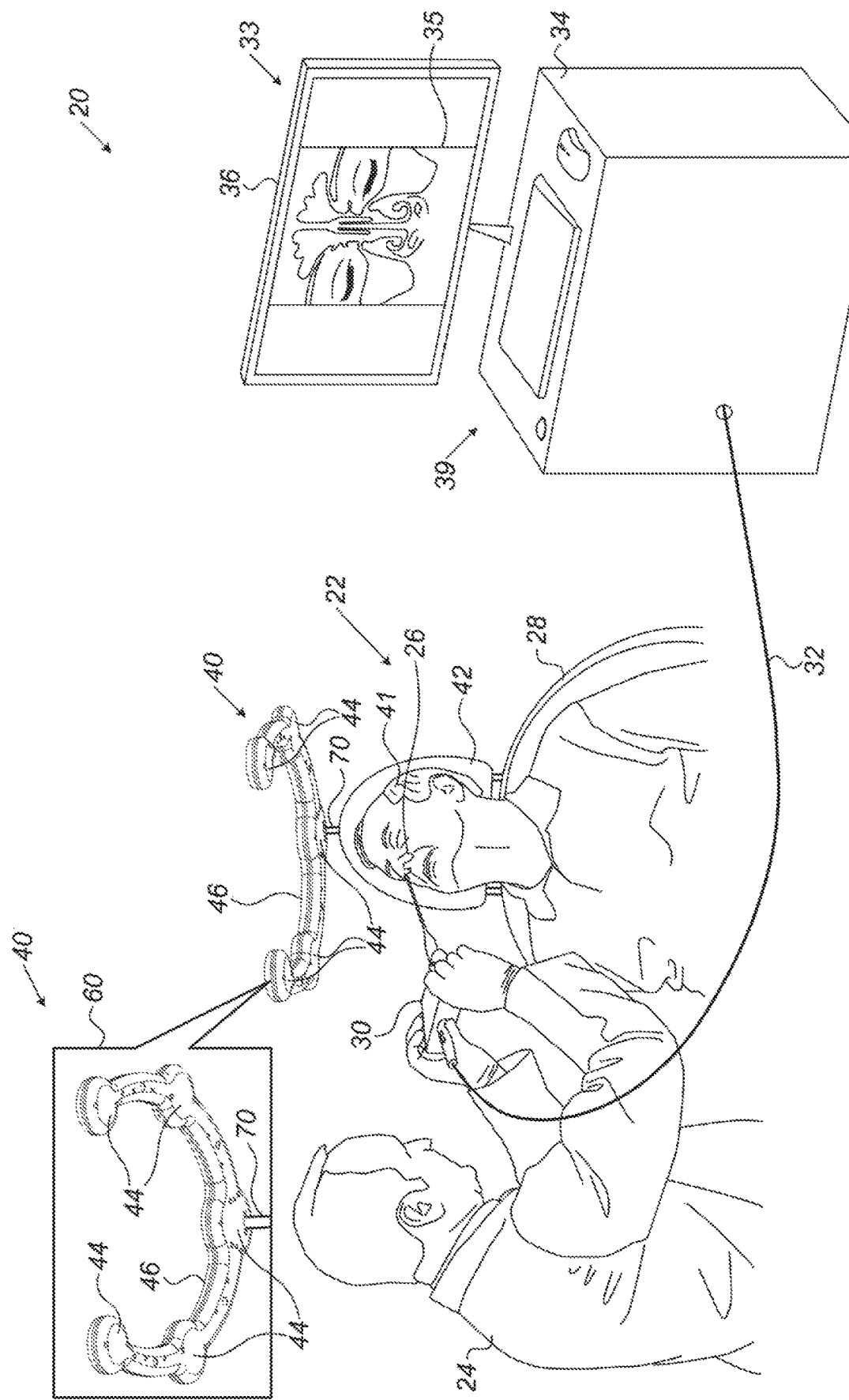
FIG. 1 is a schematic, pictorial illustration of a sinuplasty surgical system, in accordance with an embodiment of the present invention.

FIG. 1 is a schematic pictorial illustration of a sinuplasty surgical system 20, in accordance with an embodiment of the present invention. System 20 comprises a magnetic position tracking system (not shown), which is configured to track the position of one or more position sensors in a head 41 of a patient 22.

In some embodiments, the magnetic position tracking system comprises magnetic field-generators 44 and one or more position sensors (not shown). The position sensors generate position signals in response to sensing external magnetic fields of field-generators 44, thereby enabling a processor 34 to map the position of each sensor in the coordinate system of the position tracking system as will be described below.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1 (now U.S. Pat. No. 6,690,963), 2003/0120150 A1 (now U.S. Pat. No. 7,729,742), and 2004/0068178 A1 (now abandoned), whose disclosures are all incorporated herein by reference.

In the present example, system 20 comprises a location pad 40, which is mounted on a chair 28 using a mounting fixture. In the present example the mounting fixture comprises a mounting pole 70, although other suitable types of mounting fixtures can also be used. In an embodiment, pole is configured to mount location pad above patient head 41, which is placed on a pillow 42 of chair 28. In this configuration, pillow 42 and patient head 41 interpose between location pad 40 and chair 28.

Reference is now made to an inset 60, which is a view of location pad 40 from a tilted perspective. In the present example, system 20 comprises location pad 40, which is mounted on a chair 28 using a mounting pole 70. In an embodiment, pole 70 is configured to hold the location pad above patient head 41, which is placed on a pillow 42 of chair 28. In this configuration, pillow 42 and patient head 41 interpose between location pad 40 and chair 28.

In some embodiments, location pad 40 comprises multiple field-generators 44 fixed on a frame 46. In the exemplary configuration shown in FIG. 1, pad 40 comprises five field-generators 44, but any other suitable number of generators 44 can be used. In an embodiment, generators 44 are located at fixed, known positions external to the patient. System 20 further comprises a console 33, which comprises a driver circuit (not shown) configured to drive field-generators 44 with suitable signals so as to generate magnetic fields in a predefined working volume around head 41.

In an embodiment, console 33 comprises a display 36, which is configured to display an anatomical image 35 obtained using an external imaging system, such as a computerized tomography (CT) system (not shown).

In some embodiments, system 20 comprises a sinuplasty tool 30, such as a diagnostic and/or surgical tool, inserted by a physician 24 through a nose 26 of patient 22. Tool 30 is used to carry out the sinuplasty procedure in patient head 41.

In an embodiment, a position sensor (not shown) is coupled to a distal end of tool 30. The position sensor is configured to generate position signals indicative of the position of the distal end of tool 30 in the coordinate system of the magnetic position tracking system.

In an embodiment, processor 34 is configured to register image 35 with the coordinate system of the position tracking system. The registration process is typically performed before the actual sinuplasty procedure.

In some embodiments, during the sinuplasty procedure, physician 24 inserts tool 30 into head 41. Since the CT image is already registered with the position-tracking system, physician 24 may navigate the medical device whose distal end is displayed on image 35, to a desired location in head 41.

In alternative embodiments, instead of receiving image 35 from the CT, processor 34 is configured to receive one or more images acquired using another suitable anatomical imaging technique, such as fluoroscopy or magnetic resonance imaging (MRI), and to register these anatomical images with the coordinate system as described above.

Chair 28 typically comprises several parts, such as a base of the chair, adjustable headrest, backrest, seat and their respective motors, of which one or more parts are metallic. In case the location pad would be positioned under the patient's head, these metallic parts would interfere with the magnetic fields generated by field-generators 44 of location pad 40, and therefor degrade the positioning accuracy.

In some embodiments, location pad 40 is fitted above head 41, so as to set it at sufficiently large distance from the metallic parts of chair 28 to avoid interference, and yet keep it in close proximity to the position sensor coupled to tool 30. For example, pole 70 is configured to hold location pad 40 above patient head 41 at a distance larger than 5 cm from metallic objects, such as metallic objects of pillow 42 and chair 28, so as to reduce the level of interference to the magnetic fields produced by field-generators 44, without negatively impacting the positioning accuracy of the position tracking system. Note that pole 70 is configured to adjust the distance between pad 40 and metallic objects, to any suitable value that provides a desired combination of sufficient illumination and positioning accuracy, at sufficiently reduced interference.

In an embodiment, processor 34 is typically a general-purpose computer comprising suitable front end and interface circuits for receiving data from external sources, as well as measurements from the position sensor of tool 30, via a cable 32, and for controlling other components of system 20. Console 33 further comprises input devices 39 and a user display 36, which is configured to display the data.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Figure 2:
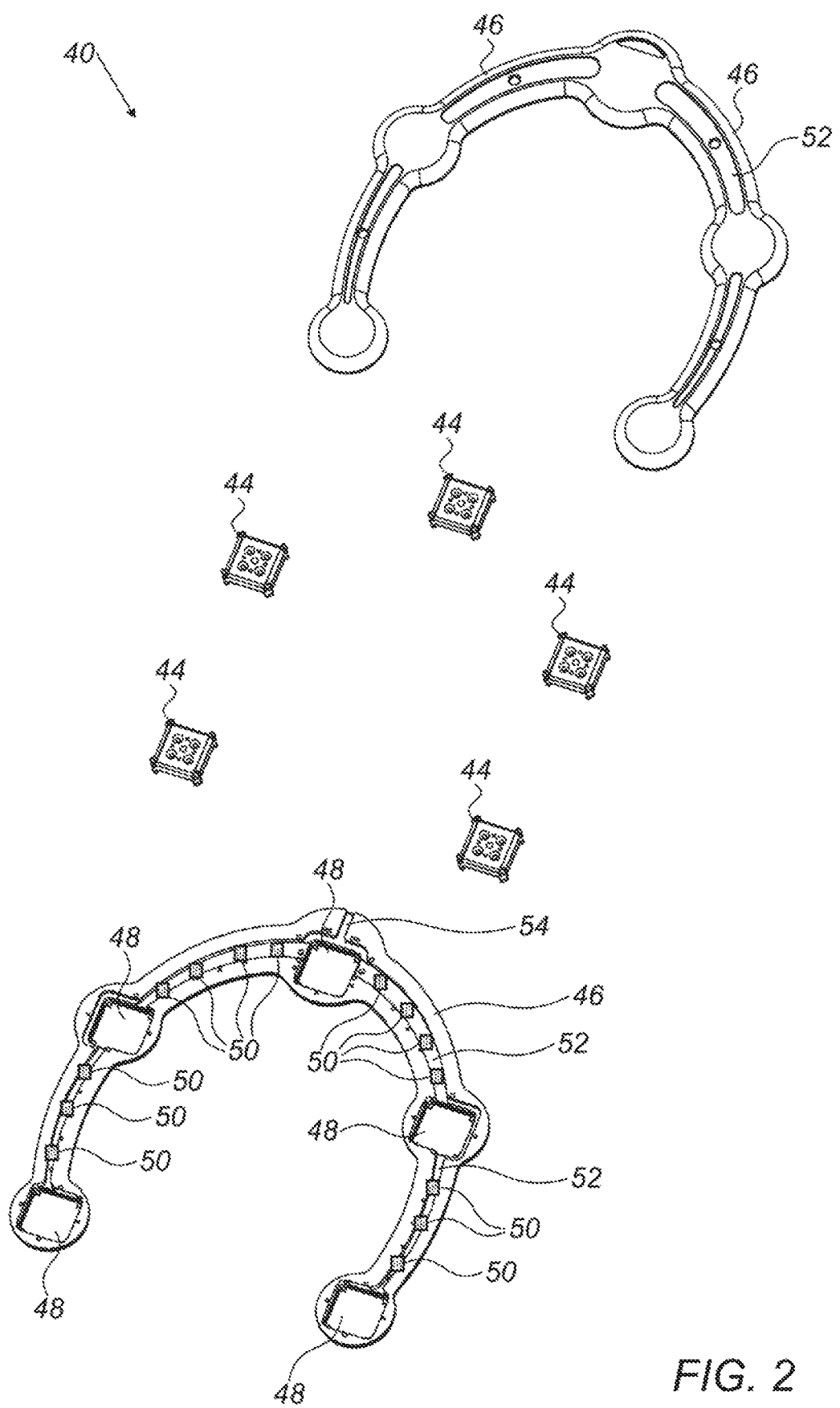
FIG. 2 is a schematic, exploded view of a location pad for sinuplasty procedures, in accordance with an embodiment of the present invention.

Ear-Nose-Throat (ENT) Location Pad Having Improved Resiliance Against Magnetic Interference FIG. 2 is a schematic, exploded view illustration of location pad 40, in accordance with an embodiment of the present invention. The upper and lower parts of location pad 40 are shown in the upper and lower parts of FIG. 2, respectively.

In some embodiments, five field generators 44 are fitted into five respective recesses 48 of frame 46.

In an embodiment, frame 46 comprises illumination elements 50, such as one or more light emitting diodes (LEDs), fitted in one or more trenches 52 formed in frame 46. In some embodiments, illumination elements 50 are adapted to illuminate head 41 of patient 22, so as to assist physician 24 in carrying out the sinuplasty procedure.

In some embodiments, one or more conducting cables (not shown) are threaded through a trench 54 of frame 46, so as to conduct signals to field-generators 44 and to illumination elements 50. The cables are fitted into trenches 52, and are configured to conduct electrical signals to field-generators 44 and to illumination elements 50.

In some embodiments, field-generators 44 are configured to operate using alternating current (AC) signals at a selected frequency, such as 17-19 kilohertz (KHz). These operating frequencies are used by the magnetic position tracking system to track the position sensor coupled to the distal end of tool 30.

The magnetic fields produced by field-generators 44 are subject to external and internal interferences that may negatively impact the positioning accuracy of the position tracking system. The term "external interference" refers to interference caused by elements that are external to the structure of location pad 40, whereas the term "internal interference" refers to interference caused by elements that are part of the structure of location pad 40.

For example, the metal parts of chair 28 may cause (external) interference to the magnetic field produced by field-generators 44. In some embodiments, pole 70 is configured to mount location pad 40 at a given distance from the metallic parts of chair 28, so that pillow 42 and patient head 41 interpose between location pad 40 and chair 28, thereby further reducing the level of interference caused by the metallic parts of chair 28.

In some cases, the configuration of location pad 40 may cause internal interference. For example, illumination elements 50, such as LEDs, typically comprise metal parts that may interfere with the AC fields applied by field-generators 44. The LEDs are typically operated by direct current (DC) signals that do not interfere with the AC signals transmitted by field-generators 44.

During operation, field-generators 44 receive power from the drive circuit of console 33, and may heat up during operation. In some embodiments, frame 46 comprises a transparent material having low thermal expansion coefficient, such as Perspex®, having thermal expansion coefficient of $75*10^{-6}$ [1/° K].

In this configuration, frame 46 exhibits an unnoticeable level of deformation even when the temperature of field-generators 44 increases to 100° C. For example, at 100° C. a deformation level of up to 0.84 mm is expected at each edge of a 300 mm long frame (i.e., extending 150 mm to each side of pole 70.)

In other embodiments, frame 46 may comprise any other suitable transparent material having thermal expansion coefficient higher than $74*10^{-6}$ [1/° K].

In some embodiments, location pad 40 is calibrated before applying the sinuplasty procedure, so as to compensate for the internal interferences caused by the metallic parts of illumination elements 50. In some embodiments, during the calibration, location pad 40 is activated the distribution of the magnetic field along the entire length of location pad 40 is measured, e.g., by a scanning robot or any other suitable means. In some embodiments, processor 34 is configured to convert these magnetic field measurements into a three-dimensional (3D) calibration map. In this embodiment, during the sinuplasty procedure processor 34 applies the 3D map so as to compensate for the internal interference caused to the magnetic fields of location pad 40.

In alternative embodiments, the disclosed techniques can be used, mutatis *mutandis*, in various other medical procedures applying magnetic position tracking techniques.

Although the embodiments described herein mainly address sinuplasty procedures, the methods and systems described herein can also be used in other applications, such as neuro-surgery, Ear-Nose-Throat (ENT), Cardiology, ophthalmology, or in any other minimally invasive procedure that applies magnetic position tracking techniques.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A location pad, comprising:
   (a) multiple field-generators, which are configured to generate respective magnetic fields in a region-of-interest of a patient body, for measuring a position of a medical instrument in the region-of-interest;
   (b) a frame, which is configured to fix the multiple field-generators at respective positions surrounding the region-of-interest such that each field-generator of the multiple field-generators is fixed against movement relative to the other field-generators of the multiple field generators, wherein the entire frame is horseshoe-shaped;
   (c) a patient support comprising a headrest and at least one metallic part; and
   (d) a mounting fixture configured to vertically position the frame in a horizontal orientation above both the headrest and a head of the patient and thereby support the frame above the head of the patient without being supported by the patient body, wherein the mounting fixture comprises a non-metallic material, wherein the frame is positioned at a distance greater than 5 cm from each metallic part of the at least one metallic part.

2. The location pad according to claim 1, and comprising one or more illumination elements, which are mounted in the frame and are configured to illuminate the patient body.

3. The location pad according to claim 2, wherein each of the illumination elements comprises one or more light emitting diodes (LEDs).

4. The location pad according to claim 1, wherein the frame comprises transparent material.

5. The location pad according to claim 1, wherein the frame comprises transparent material having expansion coefficient higher than $74*10^{-6}$ [1/° K].

6. The location pad according to claim 1, wherein the frame comprises:
 (i) a first surface facing upwardly,
 (ii) a second surface facing downwardly,
 (iii) a third surface facing radially inwardly, and
 (iv) a fourth surface facing radially outwardly,
 wherein each field-generator of the multiple field-generators is positioned on at least one of the first or second surfaces.

7. The location pad according to claim 1, wherein the frame comprises:
 (i) a first portion, wherein the first portion is horseshoe-shaped, and
 (ii) a second portion overlying the first portion, wherein the second portion is horseshoe-shaped,
 wherein each field-generator of the multiple field-generators is captured between the first and second portions of the frame.

8. The location pad according to claim 1, wherein the frame defines a plane, wherein each field-generator of the multiple field-generators is oriented to be parallel with the plane.

9. A method for producing a location pad, the method comprising:
 (a) providing multiple field-generators, which generate respective magnetic fields in a region-of-interest of a patient body, for measuring a position of a medical instrument in the region-of-interest;
 (b) fixing the multiple field-generators on a frame having a horseshoe-shape, at respective positions surrounding the region-of-interest, such that each field-generator of the multiple field-generators is fixed against movement relative to the other field-generators of the multiple field generators; and
 (c) positioning the entire frame, in a horizontal orientation, spaced apart from the patient body and above both a head of the patient and a patient support supporting the head of the patient, using a mounting fixture such that the mounting fixture and the frame are spaced apart from the patient body, wherein the patient support comprises at least one metallic part, wherein the frame is positioned a distance greater than 5 cm from each metallic part of the at least one metallic part.

10. The method according to claim 9, and comprising mounting in the frame, one or more illumination elements for illuminating the patient body.

11. The method according to claim 10, wherein each of the illumination elements comprises one or more light emitting diodes (LEDs).

12. The method according to claim 9, wherein the frame comprises transparent material.

13. The method according to claim 9, wherein the frame comprises transparent material having expansion coefficient higher than $74*10^{-6}[1/° K]$.

14. The method according to claim 9, further comprising positioning the patient body on a chair of the patient support.

15. A system including a location pad, the location pad comprising:
 (a) multiple field-generators, which are configured to generate respective magnetic fields in a region-of-interest of a patient body, for measuring a position of a medical instrument in the region-of-interest,
 (b) a frame having a horseshoe shape, which is configured to fix the multiple field-generators at respective positions surrounding the region-of-interest such that each field-generator of the multiple field-generators is fixed against movement relative to the other field-generators of the multiple field generators,
 (c) a mounting fixture, wherein the mounting fixture is configured to position the frame, in a horizontal orientation, vertically above a patient head, during a procedure, the region-of-interest being within the patient head; and
 (d) a patient support comprising a headrest, wherein the patient support includes at least one metallic part, wherein the frame is positioned at a distance greater than 5 cm from each metallic part of the at least one metallic part, wherein the mounting fixture is configured to position the frame vertically above the headrest of the patient support.

16. The system according to claim 15, further comprising one or more illumination elements mounted in the frame and configured to illuminate the patient head.

17. The system according to claim 15, further including a patient support, wherein the patient support includes a pillow, wherein the mounting fixture is secured to the pillow.

18. The system according to claim 17, wherein the mounting fixture is configured to position the frame spaced near the patient head resting on the pillow.

* * * * *